US005108373A

United States Patent [19]
Bancsi et al.

[11] Patent Number: 5,108,373
[45] Date of Patent: Apr. 28, 1992

[54] INTRAVENOUS METERING DEVICE

[75] Inventors: Joseph Bancsi, Vernon Hills; Dan Hamilton, Hoffman Estates; Ken Lynn, McHenry; Roberta Scola, Elk Grove, all of Ill.

[73] Assignee: Baxter International Inc., Deerfield, Ill.

[21] Appl. No.: 411,789

[22] Filed: Sep. 25, 1989

[51] Int. Cl.$^5$ .............................................. A61M 1/00
[52] U.S. Cl. ...................................... 604/153; 604/247; 128/DIG. 12
[58] Field of Search .............. 604/51, 56, 65, 66, 604/118, 246, 247, 257, 258, 151, 153; 128/DIG. 12

[56] References Cited

U.S. PATENT DOCUMENTS

| | | | |
|---|---|---|---|
| 2,867,213 | 1/1959 | Thomas, Jr. | 604/247 |
| 3,039,399 | 6/1962 | Everett | 604/153 X |
| 3,542,026 | 11/1970 | Bledsoe | 604/247 X |
| 3,675,891 | 7/1972 | Reynolds et al. | 251/117 |
| 4,140,118 | 2/1979 | Jassawalla . | |
| 4,245,636 | 1/1981 | Sparks et al. | 128/214 |
| 4,300,552 | 11/1981 | Cannon | 604/65 |
| 4,336,800 | 6/1982 | Giovanni | 128/214 |
| 4,411,603 | 10/1983 | Kell | 417/479 |
| 4,444,546 | 4/1984 | Pazemenas | 417/12 |
| 4,453,931 | 6/1984 | Pastrone | 604/153 |
| 4,453,932 | 6/1984 | Pastrone | 604/153 |
| 4,457,753 | 7/1984 | Pastrone | 604/153 |
| 4,464,172 | 8/1984 | Lichtenstein | 604/65 |
| 4,468,222 | 8/1984 | Lundquist | 604/153 |
| 4,470,758 | 9/1984 | Pazemenas et al. | 417/63 |
| 4,474,309 | 10/1984 | Solomon | 222/1 |
| 4,479,761 | 10/1984 | Bilstad et al. | 417/395 |
| 4,519,792 | 5/1985 | Dawe | 604/152 |
| 4,557,725 | 12/1985 | Heyne et al. | 604/67 |
| 4,594,058 | 6/1986 | Fischell | 417/413 |
| 4,642,098 | 2/1987 | Lundquist | 604/123 |
| 4,668,231 | 5/1987 | de Vries et al. | 604/891 |
| 4,696,671 | 9/1987 | Epstein et al. . | |
| 4,781,674 | 11/1988 | Redmond et al. | 604/9 |
| 4,781,675 | 11/1988 | White | 604/10 |
| 4,838,865 | 6/1989 | Flank et al. | 604/118 |
| 4,865,584 | 9/1989 | Epstein et al. | 604/67 |
| 4,867,740 | 9/1989 | East | 604/9 |
| 4,927,411 | 5/1990 | Pastrone et al. | 604/65 |

Primary Examiner—John D. Yasko
Assistant Examiner—Adam J. Cermak
Attorney, Agent, or Firm—Paul E. Schaafsma; Amy L. H. Rockwell; Paul C. Flattery

[57] ABSTRACT

An intravenous metering device is provided which includes an air retention chamber in downstream fluid communication with a source of fluid and in upstream fluid communication with a pumping chamber. A first valve is provided between the air retention chamber and the pumping chamber to control access to the pumping chamber. A second valve is provided to control the exit of fluid from the pumping chamber. The valves include a shared diaphragm portion.

17 Claims, 4 Drawing Sheets

INTRAVENOUS METERING DEVICE

FIELD OF THE INVENTION

The present invention relates in general to intravenous metering devices and in particular to an intravenous metering device utilizing an improved check valve.

BACKGROUND OF THE INVENTION

Considerable attention in recent years has been directed to the intravenous delivery of fluids such as saline solutions and the like to patients. Initially, these fluids were administered to the patient by means of gravity flow from a container holding the fluid to be delivered. Gravity-flow devices, however, can be cumbersome to use, inasmuch as pressure sufficient to sustain fluid movement in a gravity-flow device often required positioning of the device at a considerable elevation above the patient receiving the fluid. Moreover, attempts to accurately regulate the amount of fluid administered by gravity-flow devices were often unsuccessful because of the fact that the gravity-induced pressure responsible for moving fluid through the device generally decreased during the intravenous delivery operation as the fluid level within the container holding the fluid dropped.

In order to provide for improved flow of fluids to patients, pumping devices have been utilized such as found in U.S. Pat. Nos. 4,336,800; 4,453,931; 4,453,932; and 4,457,753. Such pumping devices employ a metering device control unit into which an intravenous metering device is placed. The intravenous metering device includes a pumping chamber which includes a reciprocal diaphragm. The metering device includes a pumping piston which reciprocates the diaphragm thereby changing the volume of the pumping chamber. Check valves are positioned at the pumping chamber inlet and outlet to regulate the flow of fluid and a gas retention chamber is provided upstream of the pumping chamber and the pumping chamber inlet. The gas retention chamber is connected via tubing to a fluid source while the pumping chamber outlet is connected to a patient.

The intravenous metering devices found in these patents all employ complex structure including a biased ball check valve. While such check valve performs adequately, the multiplicity of moving parts is undesirable due to cost factors and the variation in functionality associated with manufacturing complexity. What is thus needed is an intravenous metering device which improves on the use of such biased ball check valve.

BRIEF SUMMARY OF THE INVENTION

The present invention provides an intravenous metering device which includes a pumping chamber and means for varying the volume of the pumping chamber. In a preferred embodiment, the pumping chamber includes a reciprocating diaphragm with the volume varying means reciprocating the diaphragm to provide the pumping action. The pumping chamber includes an inlet having a first valve to control the entry of fluid into the fluid pumping chamber and an outlet with a second valve to control the exit of fluid from the pumping chamber. An air retention chamber is also provided upstream of the pumping chamber to ensure that the fluid entering the pumping chamber is free of air bubbles. The air retention chamber is in fluid communication with a source of fluid while the outlet of the pumping chamber is connected to a patient.

The first valve includes a flexible diaphragm which in a relaxed position opens the inlet and in a stressed position closes the inlet. The second valve includes a diaphragm which is normally in a closed position but which can be stressed into an open position. In the preferred embodiment of the present invention, the pumping chamber diaphragm, the first valve diaphragm, and the second valve diaphragm utilize an integral diaphragm. By use of these two valves, an intravenous metering device is provided which improves on the intravenous metering devices of the prior art.

DETAILED DESCRIPTION OF A PREFERRED EMBODIMENT

Figure 1:
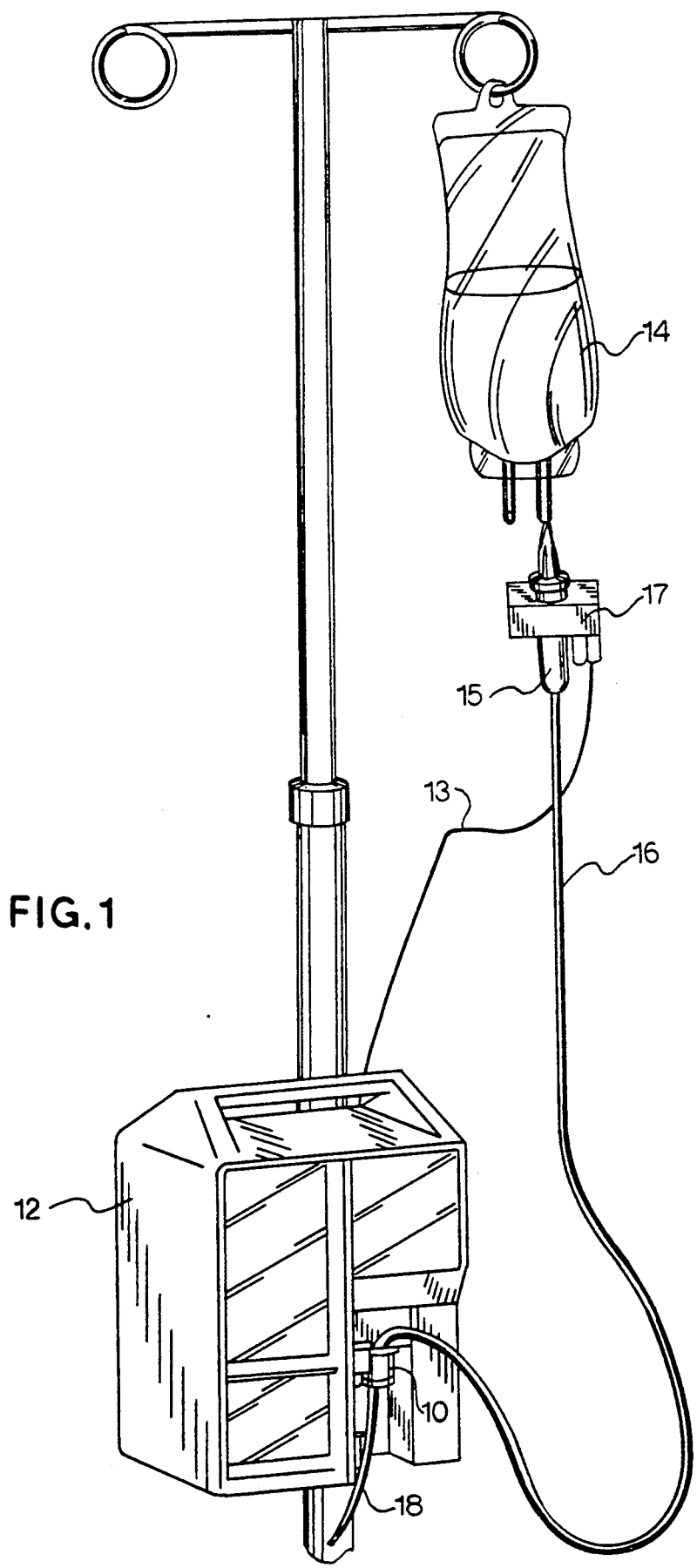
FIG. 1 is a perspective view illustrating the use of an intravenous metering device in accord with the principles of the present invention.

Referring first to FIG. 1, an intravenous metering device 10 is shown positioned within a metering device control unit 12. The intravenous metering device 10 in conjunction with the metering device control unit 12 acts as a pump means to transfer fluid from a source of fluid 14 to a patient. The intravenous metering device 10 is connected to the source of fluid 14 by means of conventional tubing 16. Additional tubing 18, extending from the outlet of intravenous metering device 10, transfers precise amounts of fluid to the patient.

Provided between the container of fluid 14 and the tubing 16 is a conventional drip chamber 15. The drip chamber 15 is partially surrounded by a drop sensing means 17 which senses the drops passing in the drip chamber 15. The drop sensing means 17 is connected to the metering device control unit 12 by wiring 13 so that, if the absence of drops is sensed, an alarm in the metering device control unit 12 can be sounded.

Figure 2:
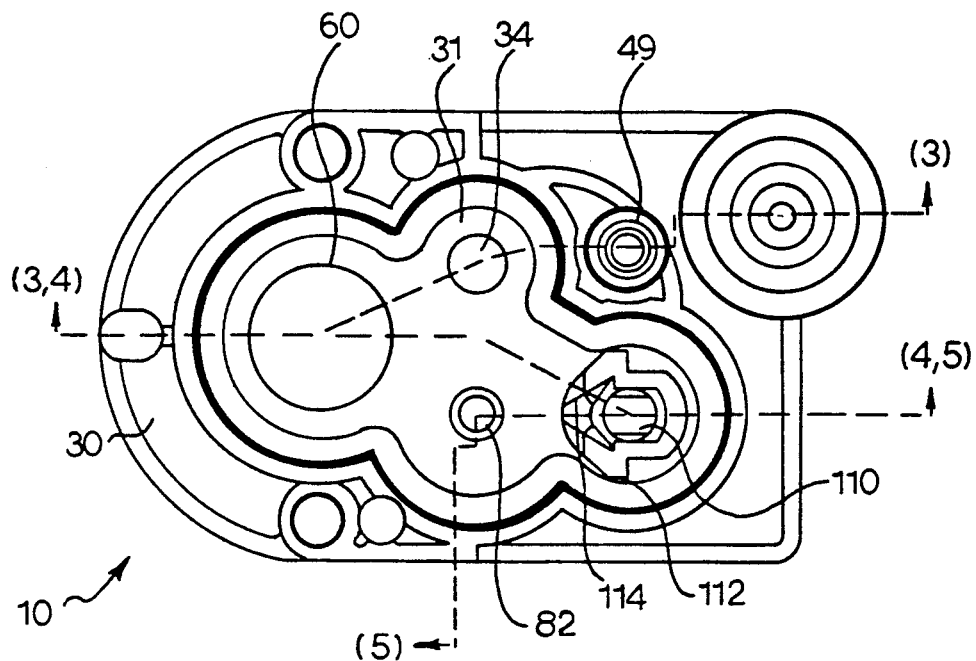
FIG. 2 is a top view showing an intravenous metering device in accord with the principles of the present invention.
Figure 3:
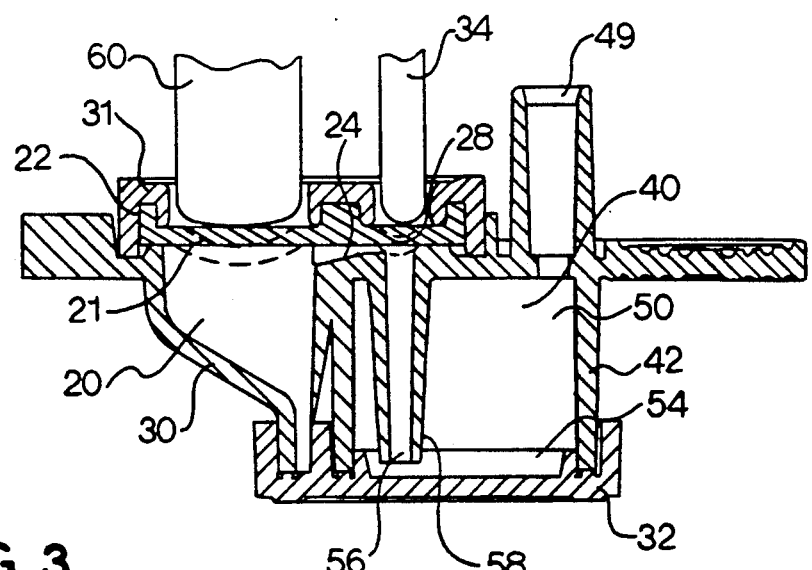
FIG. 3 is a cross-sectional view of the device of FIG. 2 taken along line III—III of FIG. 2.
Figure 4:
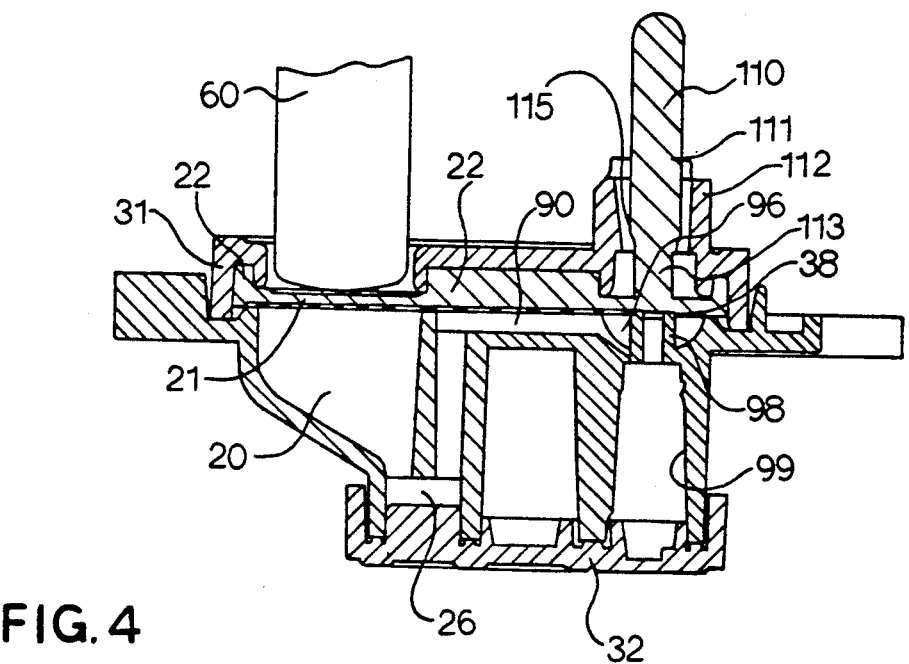
FIG. 4 is a cross-sectional view of the device of FIG. 2 taken along line IV—IV of FIG. 2.

Referring now to FIGS. 2 thru 5, construction of an intravenous metering device 10 in accord with the principles of the present invention is shown in detail. The intravenous metering device 10 includes a pumping chamber 20 formed in housing 30 and a flexible diaphragm 22 which forms an upper portion 21 of pumping chamber 20. The housing 30 includes a housing lid 31 as well as a housing bottom 32. A pumping chamber inlet 24 and a pumping chamber outlet 26 are formed in pumping chamber 20. Pumping chamber 20 includes a valve seat means 28. Valve actuator 34 controls the admission of fluid into pumping chamber 20 by reciprocating the diaphragm 22 between an open position, shown in solid lines in FIG. 3, and a closed position as shown by dotted lines in FIG. 3. As best seen in FIG. 4, the pumping chamber outlet 26 includes a valve 38 which is normally held in a closed position.

Intravenous metering device 10 further includes a metering device inlet 49 which is disposed above an air retention chamber 40 bounded by housing sidewalls 42. The air retention chamber 40 is of sufficient size to include an air retention chamber upper portion 50 providing for an air-fluid interface. Air retention chamber 40 also includes an air retention chamber lower portion 4 which collects fluid free of air bubbles. The fluid free of air bubbles can then pass through an air retention chamber passageway 56 in tubular conduit 58 past the open valve seat means 28 and on into the pumping chamber 20.

The metering device control unit 12 provides means for varying the volume of the pumping chamber 20 in order to pressurize the pumping chamber 20 to provide fluid propulsion. These means can include means for flexing diaphragm 22 into pumping chamber 20 which in the present invention is a reciprocating pumping piston 60 which presses against flexible diaphragm 22, whereupon fluid free of air bubbles is pumped through the intravenous metering device 10 as described below. The position of diaphragm 22 shown by solid lines in FIG. 3 illustrates the condition of the diaphragm 22 when pumping piston 60 is in the upstroke position while the dotted line position of diaphragm 22 illustrates the position of the diaphragm 22 in the associated down-stroke position of pumping piston 60.

It is important to measure the pressure of fluid downstream or distal of the intravenous metering device 10. Excessive distal pressure may indicate a plugged filter or distal line occlusion. Accordingly, the intravenous metering device 10 of the present invention includes a pressure indicating means for determining distal pressure. This pressure indicating means includes a pressure measuring chamber seen in FIG. 5.

The distal pressure measuring chamber itself is incorporated into the fluid flow path leaving the pumping chamber 20 so that priming will be accomplished in generally the same manner as with the pumping chamber 20. Intravenous metering device 10 is constructed with a distal pressure measuring chamber 70 and an intravenous metering device outlet 72 positioned at the base of distal pressure measuring chamber 70. An intermediate passageway 74 is formed to carry fluid from the pumping chamber outlet 26 past valve 38 into the distal pressure measuring chamber 70 entering at a distal pressure inlet 78. The intravenous device outlet 72 is located at the bottom of distal pressure measuring chamber 70 so that the distal pressure measuring chamber 70 is made a part of the fluid flow path through intravenous metering device 10. The flow of the fluid during the intravenous metering device 10 priming operation described below will continue on into the distal pressure measuring chamber 70, removing air otherwise present in the intravenous metering device 10 from the distal pressure measuring chamber 70 as well as the pumping chamber 20.

Distal pressure pin 82 is oriented over a portion 80 of diaphragm 22 which covers the distal pressure measuring chamber 70 as shown, and movement of distal pressure pin 82 in response to upward motion of diaphragm portion 80 can be translated into a distal pressure reading by employing a measuring device which measures the movement of distal pressure pin 82. Also, as seen in FIG. 4, the shifting of the intravenous metering device elements in order to incorporate the distal pressure measuring chamber 70 results in the placement of valve 38 at a location somewhat remote from pumping chamber 20. An elongated passageway 90 is therefore formed in the intravenous metering device 10 to transport fluid from the pumping chamber 20 to the valve 38.

Figure 6A:
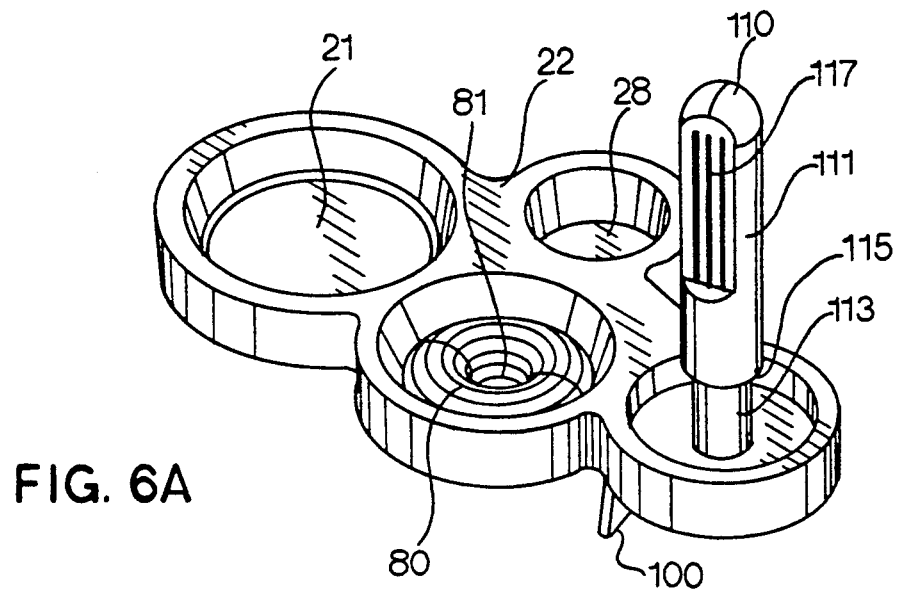
FIG. 6A is an upper perspective view of the diaphragm device of the present invention.
Figure 6B:
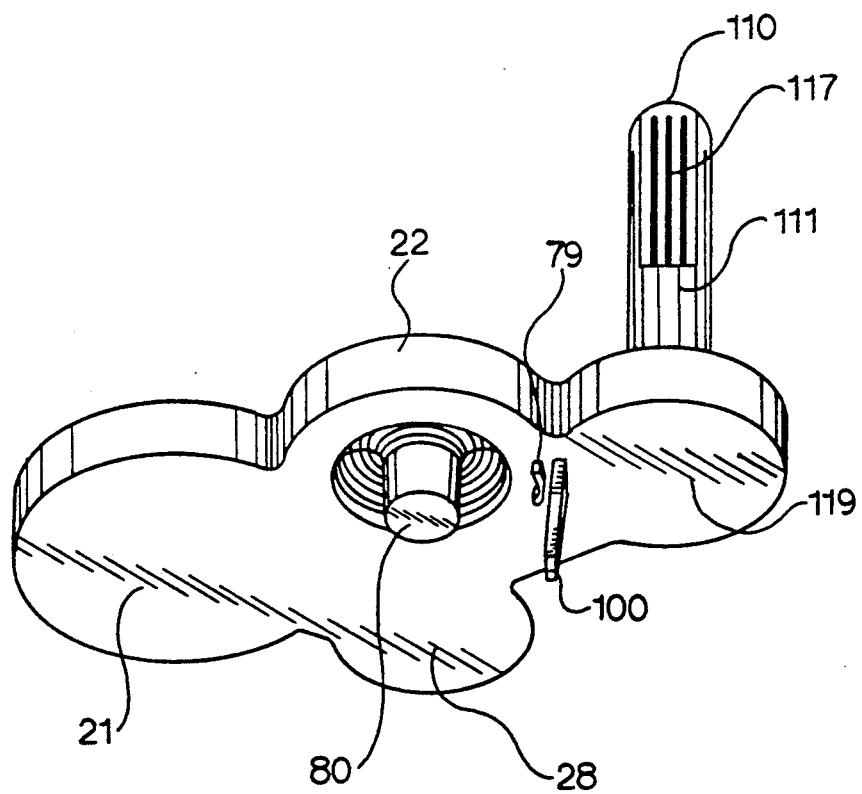
FIG. 6B is a lower perspective view of the diaphragm device of the present invention.

Referring to FIGS. 6A and 6B, a perspective view of the diaphragm 22 is seen in detail, both from above and below. The diaphragm 22 includes the upper portion 21 of pumping chamber 20 which is reciprocable by pumping piston 60 to vary the volume of the pumping chamber 20. The diaphragm 22 also includes the upper portion 80 of the distal pressure measuring chamber 70. This portion 80 of the diaphragm 22 includes a generally funnel shaped aperture 81 into which distal pressure pin 82 is held.

Diaphragm 22 further includes valve seat means 28 which, in conjunction with housing 30, forms pumping chamber inlet 24. Valve seat means 28 is reciprocable by valve activator 34 to control admission of fluid into pumping chamber 20.

Extending upwardly from the diaphragm 22 is the integrally formed priming stem 110. The priming stem 100 includes an increased diameter portion 111 and a stem base 113. The junction of the increased diameter portion 111 and stem base 113 defines a stem flange 115. The priming stem 110 further includes a grip portion 117 to aid in user gripping. On the diaphragm opposite the primary stem is standpipe contacting portion 119 which establishes contact with standpipe 98.

Figure 5:
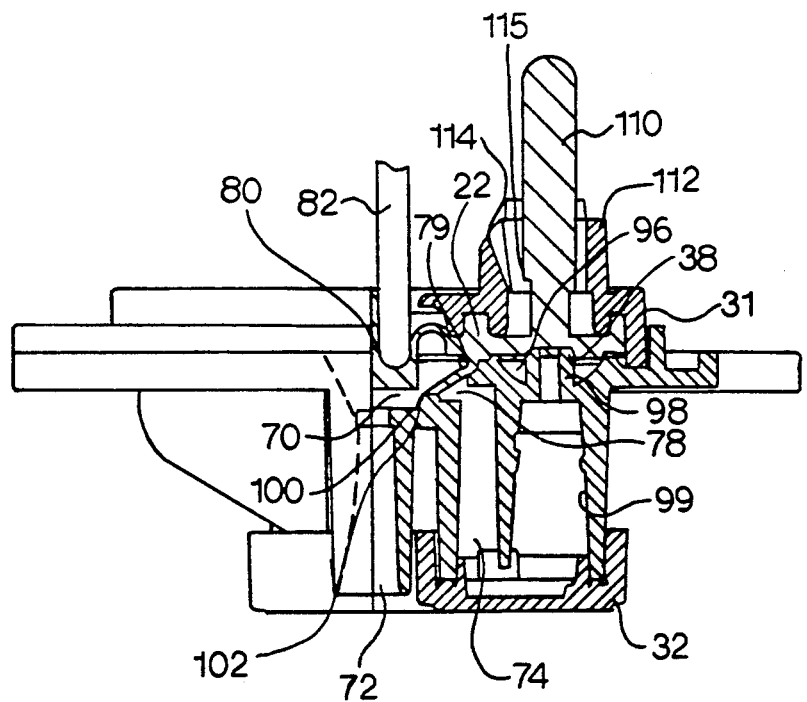
FIG. 5 is a cross-sectional view of the device of FIG. 2 taken along line V—V of FIG. 2.

Extending downwardly from the diaphragm 22 is an integrally formed flapper valve 100 which forms with a molded ramp 102 on housing 30 a one-way valve. This one-way valve separates the intermediate passageway 74 from the distal pressure measuring chamber 70. Also extending downwardly is a biasing ridge 79 which acts to bias flapper valve 100 against molded ramp, as seen in FIG. 5.

Referring back to FIGS. 2-5, operation of the device will be described. When pressure is applied to the pumping chamber 20 by the pumping piston 60, the fluid flows from the pumping chamber 20 through the pumping chamber outlet to the elongated passageway 90. An annular outlet pressure chamber 96 is formed at the downstream end of elongated passageway 90 having as its upper wall the diaphragm 22. A standpipe 98 having an aperture 99 defined along its central axis is centered in outlet pressure chamber 96. At its upper periphery, the standpipe 98 is pre-loaded against the diaphragm 22 thus forming a fluid seal to prevent fluid flow.

When sufficient pressure is generated in pumping chamber 20 and outlet pressure chamber 96, the diaphragm 22 is lifted off the standpipe 98 thus opening valve 38. With valve 38 open, fluid passes into the intermediate passageway 74. Because air is compressed more readily than fluid, if air is trapped in the pumping chamber 20, sufficient pressure will not be generated in the pumping chamber 20 and outlet pressure chamber 96 to lift the diaphragm 22 off the standpipe 98. This disables the intravenous metering device 10 which acts as a safety means to prevent air from being pumped downstream to the patient.

From the intermediate passageway 74, the fluid enters the distal pressure measuring chamber 70. Provided at the opening to the distal pressure measuring chamber 70 is a one-way flapper valve 100 carried on a molded ramp 102 formed integrally as part of cassette housing 30. The flapper valve 100 is integrally molded as part of diaphragm 22 to be biased against the molded ramp 102. The flapper valve 100 thus acts as a valve to allow fluid to pass into the distal pressure measuring chamber 70 but to prevent fluid from flowing back into the intermediate passageway 74 and back to the pumping chamber 20. Also extending downwardly is a biased ridge 79 which acts to bias flapper valve 100 against molded ramp 102, as seen in FIG. 5.

The diaphragm 22 further includes an integrally molded priming stem 110 extending from the diaphragm 22 above the outlet valve 38 portion. The priming stem 110 includes an upper increased diameter portion 111 integrally formed with a stem base 113 thereby defining a stem flange 115. The priming stem 110 can be pulled to manually lift the diaphragm 22 off the standpipe 98 to open the pumping chamber outlet 26. In addition, formed in the housing lid surrounding the priming stem 110 is stem lock housing 112. The stem lock housing 112 includes a stem locking groove 114, best seen in FIG. 5, in which the stem flange 115 can rest. Also, as best seen in FIG. 2, the stem lock housing 112 is generally formed as an arrow to direct the user to the stem locking groove 114.

Prior to use, the intravenous metering device must be primed to eliminate air from the device. When intravenous metering device 10 is to be primed, the device is inverted, and the priming stem 110 is pulled such that the diaphragm 22 is lifted off the standpipe 98 to open the pumping chamber outlet 26 so as to allow the sequential passage of fluid from metering device inlet 49 through the air retention chamber 40 and the pumping chamber 20 to the distal pressure measuring chamber 70 to the outlet tubing 18. With the device inverted each of the chambers 20 and 40 are primed by directing the fluid into the bottom and allowing the fluid to fill the chambers upwardly. Such relatively constant fluid flow assures the elimination of air prior to use of the intravenous metering device 10, consequently enabling the intravenous metering device 10 to administer fluid free of air bubbles to a patient.

Following the priming operation, intravenous metering device 10 is returned to its upright position and inserted into metering device control device 12. Incoming fluid, transmitted by tubing 16 to the intravenous metering device inlet 49, subsequently passes into the air retention chamber 40 which, due to the downward extension of tubular conduit 58, prevents any air from entering the pumping chamber 20 and allows for the generation of a air-fluid interface in air retention chamber upper portion 50. Fluid free of air bubbles passes from the air retention chamber lower portion 54 through passageway 56. When valve actuator 34 is reciprocated upwardly, fluid free of air bubbles is allowed to pass into pumping chamber 20. Valve actuator 34 is then closed. As the flexible diaphragm 22 is moved downwardly by means of the pumping piston 60, the volume within pumping chamber 20 is decreased and the pressure within pumping chamber 20 and outlet pressure chamber 96 lifts the diaphragm 22 off the standpipe 98, thereby allowing a precise amount of metered fluid to be pumped from pumping chamber 20 through the intravenous metering device outlet 72 to a patient. The intravenous metering device 10 of the present invention may be disposable, permitting a fresh and sterilized intravenous metering device 10 to be employed for each delivery of intravenous fluid to a patient.

It should be understood that various changes and modifications to the preferred embodiments described herein will be apparent to those skilled in the art. Such changes and modifications can be made without departing from the spirit and scope of the present invention without diminishing its attendant advantages. It is therefore intended that such changes and modifications be covered by the appended claims.

What is claimed is:

1. A device which meters fluids for delivery from a source of fluid to a patient, comprising:
    an air retention chamber having upper and lower portions, the upper portion having an inlet in fluid communication with the source of fluid, the lower portion having an outlet in fluid communication with a fluid passageway;
    a pumping chamber having an inlet and an outlet, the inlet being in fluid communication with the fluid passageway, the pumping chamber inlet including a first valve means to control the entry of fluid into the pumping chamber, the pumping chamber outlet including a second valve having an outlet pressure chamber in fluid communication with the pumping chamber and having a diaphragm as an upper wall;
    a standpipe prestressed against the diaphragm; and
    means for varying the volume of the pumping chamber to pressurize the pumping chamber;
    such that in response to an increase in the pumping chamber pressure when sufficient fluid pressure is present in the outlet fluid pressure chamber the diaphragm is lifted off of the standpipe by the fluid pressure thereby opening the second valve.

2. A device according to claim 1 wherein the first valve means includes a flexible diaphragm.

3. A device according to claim 2 wherein the first valve means flexible diaphragm and the normally closed flexible diaphragm portion is the same diaphragm.

4. A device according to claim 3 wherein the diaphragm also forms a side of the pumping chamber and the means for varying the volume of the pumping chamber includes means for flexing the diaphragm into the pumping chamber.

5. A device according to claim 3 further including a distal pressure indicating means downstream of the second valve for measuring downstream fluid pressure.

6. A device according to claim 5 wherein the distal pressure indicating means includes a distal pressure measuring chamber in fluid communication with the second valve, the diaphragm forming a side of the distal pressure measuring chamber.

7. A device according to claim 1 further including means for preventing the increase in the pumping chamber from being sufficient to open the second valve when air is present in the pumping chamber.

8. A device according to claim 1 further including a one-way flapper valve provided downstream of the second valve, the one-way flapper valve preventing fluid from flowing back into the second valve.

9. A device according to claim 8 wherein the one-way flapper valve includes a flap integrally formed from the flexible diaphragm.

10. A device which meters fluids for delivery from a source of fluid to a patient, comprising:
    an air retention chamber having an inlet and an outlet, the inlet being in fluid communication with the source of fluid, the outlet being in communication with a fluid passageway;

a pumping chamber having an inlet and an outlet, the inlet being in fluid communication with the fluid passageway, the pumping chamber inlet including a first flexible diaphragm valve to control the entry of fluid into the pumping chamber, the pumping chamber outlet including a second valve having an outlet chamber in fluid communication with the pumping chamber and having a diaphragm as an upper wall;

a standpipe prestressed against the diaphragm; and means for varying the volume of the pumping chamber to pressurize the pumping chamber;

such that in response to an increase in pressure in the pumping chamber when sufficient fluid pressure is present in the outlet fluid pressure chamber the diaphragm is lifted off of the standpipe by the fluid pressure thereby opening the second valve.

11. A device according to claim 10 wherein the first flexible diaphragm valve and the second flexible diaphragm valve include the same diaphragm.

12. A device according to claim 11 wherein the diaphragm also forms a side of the pumping chamber and the means for varying the volume of the pumping chamber includes means for flexing the diaphragm into the pumping chamber.

13. A device according to claim 11 further including distal pressure indicating means downstream of the second valve for measuring downstream fluid pressure.

14. A device according to claim 13 wherein the distal pressure indicating means includes a distal pressure measuring chamber in fluid communication with the second valve, the diaphragm forming a side of the distal pressure measuring chamber.

15. A device according to claim 10 further including means for preventing the increase in the pumping chamber pressure from being sufficient to operate the normally closed diaphragm when air is present in the pumping chamber.

16. A device according to claim 10 further including a one-way flapper valve provided downstream of the second valve, the one-way flapper valve preventing fluid from flowing back into the second valve.

17. A device according to claim 16 wherein the one-way flapper valve includes a flap integrally formed from the flexible diaphragm.

* * * * *